(12) United States Patent
Chi et al.

(10) Patent No.: US 8,889,872 B2
(45) Date of Patent: Nov. 18, 2014

(54) BISAZOLE-BASED COMPOUND AND GROUP VIII TRANSITION METAL COMPLEX

(71) Applicants: Yun Chi, Hsinchu (TW); Hsiu-Hsuan Yeh, Hsinchu (TW); Shu-Te Ho, Hsinchu (TW); Shih-Han Chang, Hsinchu (TW)

(72) Inventors: Yun Chi, Hsinchu (TW); Hsiu-Hsuan Yeh, Hsinchu (TW); Shu-Te Ho, Hsinchu (TW); Shih-Han Chang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 15 days.

(21) Appl. No.: 13/668,025

(22) Filed: Nov. 2, 2012

(65) Prior Publication Data

US 2013/0296567 A1    Nov. 7, 2013

(30) Foreign Application Priority Data

May 2, 2012   (TW) ............................... 101115581 A

(51) Int. Cl.
    *C07D 215/38*    (2006.01)
(52) U.S. Cl.
    USPC ..................................................... 546/268.1
(58) Field of Classification Search
    USPC ..................................................... 546/268.1
    See application file for complete search history.

(56) References Cited

U.S. PATENT DOCUMENTS 7,538,217 B1   5/2009   Lin et al.

FOREIGN PATENT DOCUMENTS

TW    201139453 A1   11/2011

OTHER PUBLICATIONS

Yeh et al., "Thiocyanate-Free Ruthenium(II) Sensitizers with Bipyrazolate Bidentate Chelates for Dye-Sensitized Solar Cell", A-COE 2011, Taipei, Taiwan, Nov. 4-6, 2011, p. 95.

*Primary Examiner* — D M Seaman
(74) *Attorney, Agent, or Firm* — Birch, Stewart, Kolasch & Birch, LLP

(57) ABSTRACT

A bisazole-based compound is represented by formula (I):

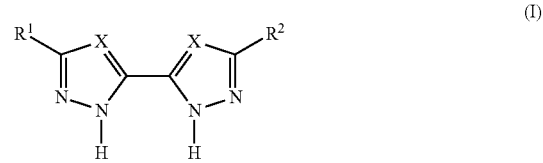

(I)

wherein X represents C—$R^3$ or nitrogen, $R^1$ and $R^2$ independently represent a haloalkyl group, $R^3$ represents H or F. A transition metal complex is represented by formula (II):

$$ML^1L^2L^3 \qquad (II)$$

wherein M is a transition metal, $L^1$ represents

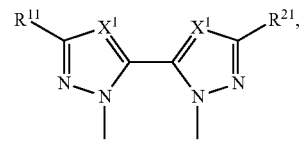

in which X represents C—$R^{31}$ or nitrogen, $R^{11}$ and $R^{21}$ independently represent a haloalkyl group, and $R^{31}$ represents H or F; and $L^2$ and $L^3$ independently represent a dipyridine-based ligand.

12 Claims, 1 Drawing Sheet

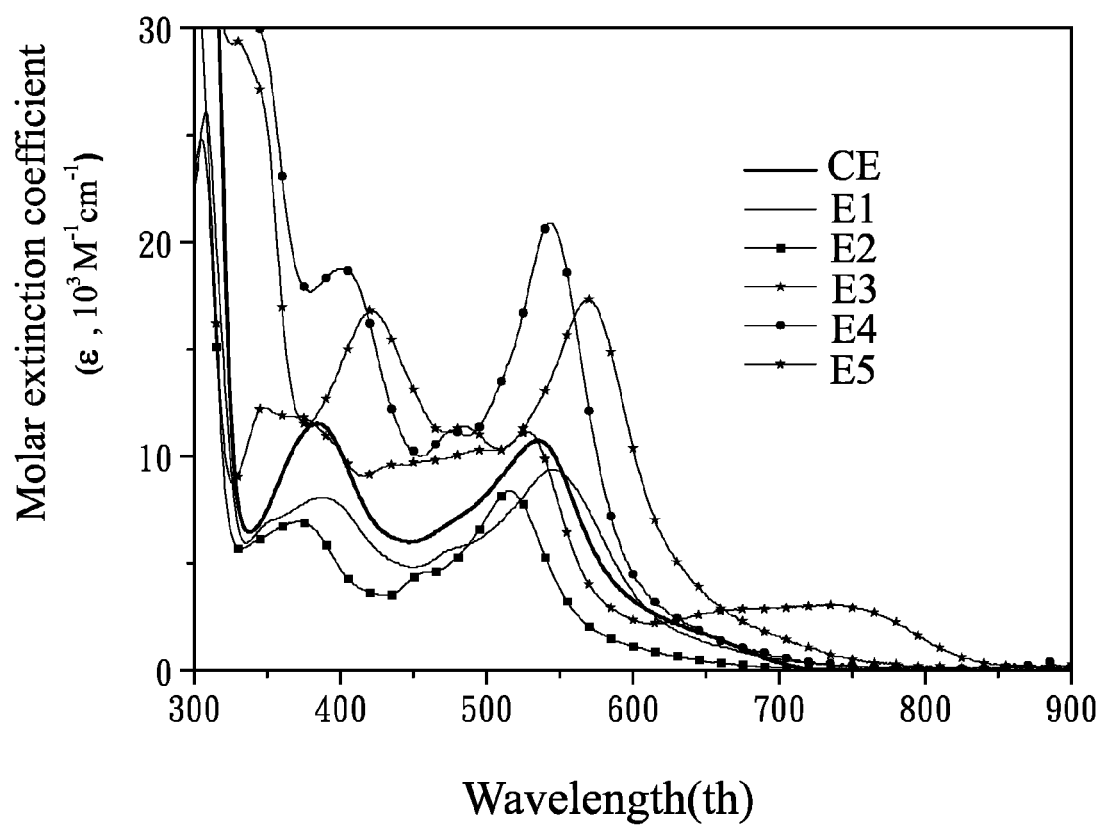

BISAZOLE-BASED COMPOUND AND GROUP VIII TRANSITION METAL COMPLEX

CROSS-REFERENCE TO RELATED APPLICATION

This application claims priority of Taiwanese application no. 101115581, filed on May 2, 2012.

BACKGROUND OF THE INVENTION

1. Field of the Invention

This invention relates to a bisazole-based compound and a Group VIII transition metal complex that is suitable to serve as a dye in a dye-sensitized solar cell, and particularly to a Group VIII transition metal complex containing a bisazole-based ligand.

2. Description of the Related Art

In recent years, solar cells have been developed with the increasing demand for energy. In particular, the dye-sensitized solar cells have shown most promise among solar cells. The dye-sensitized solar cells absorb visible light and near infrared light to excite electrons. The excited electrons are effectively transferred to a conduction band of a semiconductor in the dye-sensitized solar cells to generate a photocurrent. Therefore, the property of a dye used in the dye-sensitized solar cells will affect directly the photoelectric conversion efficiency of the dye-sensitized solar cell. At present, the ruthenium complex is the main target of research for the dye in the solar cell.

U.S. Patent Application Publication No. 2011/0277841 A1 discloses a photosensitizer represented by the following formula (a):

$$RuT^1T^2T^3 \qquad (a)$$

wherein Ru is ruthenium; $T^1$, $T^2$ and $T^3$ represent heterocyclic bidentate ligands, $T^1$ has a chemical formula represented by formula (b), $T^2$ has a chemical formula represented by formulae (b), (c), (d) or (e), and $T^3$ has a chemical formula represented by formulae (c), (d) or (e).

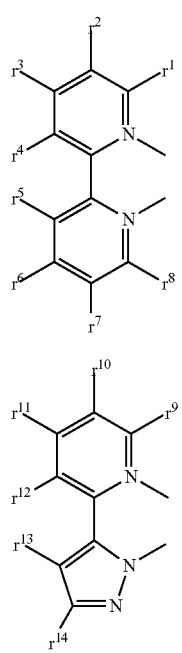

(b)

(c)

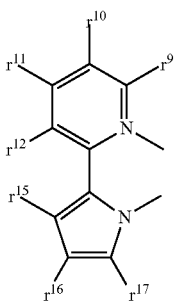

(d)

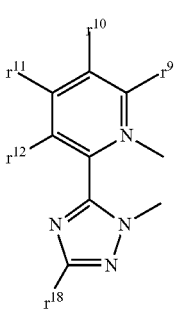

(e)

wherein, $r^1, r^2, r^3, r^4, r^5, r^6, r^7, r^8, r^9, r^{10}, r^{11}, r^{12}, r^{13}, r^{14}, r^{15}, r^{16}, r^{17}$, and $r^{18}$ are independently selected from the group consisting of hydrogen, halogen, aryl group, alkenyl group, $C_1$-$C_{20}$ alkyl group, cycloalkyl group, alkynyl group, CN, $CF_3$, alkylamino, amino, alkoxy, heteroaryl, halogen substituted aryl group, halogen substituted aromatic group, haloalkyl substituted aryl group, haloalkyl substituted aromatic group and aryl substituted $C_1$-$C_{20}$ alkyl group.

However, in the case that $T^1$ and $T^2$ of the ruthenium complex have a chemical formula represented by formula (b), the ruthenium complex is a monovalent electropositive complex that is difficult to purify and thus has a low yield.

SUMMARY OF THE INVENTION

Therefore, it is desirable to develop a neutral ruthenium complex.

According to one aspect of this invention, a bisazole-based compound is represented by formula (I):

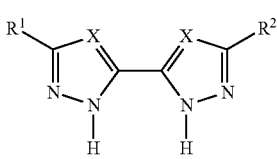

(I)

wherein X represents C—$R^3$ or nitrogen, $R^1$ and $R^2$ independently representing a haloalkyl group; $R^3$ representing H or F.

According to another aspect of this invention, a transition metal complex is represented by formula (II):

$$ML^1L^2L^3 \qquad (II)$$

wherein M is a transition metal; $L^1$ represents

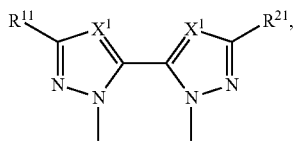

in which X represents C—$R^{31}$ or nitrogen, $R^{11}$ and $R^{21}$ independently representing a haloalkyl group; $R^{31}$ representing H or F; $L^2$ and $L^3$ independently represent a dipyridine-based ligand, and at least one of $L^2$ and $L^3$ is a dipyridine-based ligand having

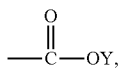

Y representing H, an alkali metal group, a $C_1$ to $C_{12}$ linear alkyl group, a $C_1$ to $C_{12}$ branched alkyl group, or $N(C_4H_9)_4^+$.

BRIEF DESCRIPTION OF THE DRAWING

Other features and advantages of the present invention will become apparent in the following detailed description of the preferred embodiments of the invention, with reference to the accompanying drawing, in which:

FIG. 1 is a graph illustrating the absorption spectrum of the ruthenium complexes of the preferred embodiments according to the present invention and the absorption spectrum of N719 dye of a comparative example.

DETAILED DESCRIPTION OF THE PREFERRED EMBODIMENTS

This invention provides a bisazole-based compound represented by formula (I):

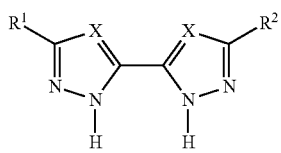

wherein X represents C—$R^3$ or nitrogen, $R^1$ and $R^2$ independently represent a haloalkyl group, and $R^3$ represents H or F.

Preferably, the haloalkyl group is a $C_1$ to $C_5$ haloalkyl group.

Preferably, the haloalkyl group is $CF_3$, $C_2F_5$, or $C_3F_7$.

More preferably, the haloalkyl group is $CF_3$.

In an embodiment of this invention, X is C—$R^3$, and $R^3$ is H.

In another embodiment of this invention, X is nitrogen.

Conventionally, most of the Group VIII transition metal complexes are ionic complexes that are liable to be left on columns while conducting purification by means of column chromatography, thereby resulting in poor purification and low yield. It is also known that complexing counterions must be added to the ionic complex in order to achieve a neutral charge balance of the ionic complex so that the ionic complex exists stably and is usable. However, since the ionic complex is liable to absorb water, when the ionic complex is applied to the dye-sensitized solar cells, cell components of the dye-sensitized solar cells may be adversely affected. In addition, the moisture may seep into the cell components so that the complexing counterions may detach from the titanium dioxide electrode surface and solve into an electrolytic solution, thereby reducing the lifespan of the solar cells.

On the contrary, after the bisazole-based compound of the present invention is bonded to a Group VIII transition metal to form a complex, the complex is capable of maintaining electric neutrality, and is relatively easy to purify and has a high yield. Therefore, the usability and the yield of the Group VIII transition metal complex of the present invention can be improved. Moreover, since the Group VIII transition metal complex of the present invention is a neutral complex and thus the complexing counterions are unnecessary, the above-mentioned problems attributed to the complexing counterions can be avoided.

In addition, by controlling the number of the nitrogen on the azolyl group of the bisazole-based compound of this invention, the energy level difference between the highest occupied molecular orbital (HOMO) and the lowest unoccupied molecular orbital (LUMO) can be adjusted, and the energy level potential of the highest occupied molecular orbital (relative to normal hydrogen electrode (NHE) potential) can be increased, for example, moved from a negative potential to a positive potential, or moved from a positive potential to a higher positive potential. Generally, the energy level potential of the highest occupied molecular orbital (relative to NHE potential) of the Group VIII transition metal complex in a dye-sensitized solar cell must be greater than the redox potential of $I^-/I_3^-$ in an electrolytic component. Based on experience, the energy level difference of the energy level potential of the highest occupied molecular orbital and the redox potential of the electrolytic component should be above at least 0.55V such that the complex may have better regeneration efficiency. For example, when the redox potential of the electrolytic component is 0.35V (relative to NHE), the energy level potential of the highest occupied molecular orbital of the complex must be at least greater than 0.9V (relative to NHE). In certain examples of the present invention, the energy level potential of the highest occupied molecular orbital of the Group VIII transition metal complex is higher than 0.90V so that the transition metal complex of this invention may have better regeneration efficiency.

Further, when the bisazole-based compound is bonded to the Group VIII transition metal, by virtue of the haloalkyl group on the bisazole-based compound, hydrogen atom on the nitrogen of the bisazole-based compound can be urged to detach and only the nitrogen that loses the hydrogen atom can be bonded to the metal so that nitrogen at the other site is unlikely to be bonded to the metal and thus no structural isomer would be formed. In addition, since the haloalkyl group on the bisazole-based compound exhibits larger spatial hindrance characteristics, the possibility of generation of the structural isomer can be reduced, thereby effectively increasing the yield of the Group VIII transition metal complex of the present invention.

The proper reactants and reaction conditions for the bisazole-based compound of the present invention may be selected based on the substituted groups of the bisazole-based compound. It should be noted that, in the chemical formula of the compound of this invention and the chemical formulae of the reactants used to prepare the compound of this invention, the same serial number has the same definition. For example, $R^1$ of a reactant (see below) has the same definition as $R^1$ in formula (I) of this invention.

Preferably, the reaction step for preparing a bisazole-based compound in which X is C—R³ comprises: reacting

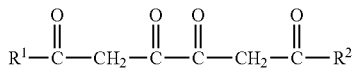

and a hydrazine compound to obtain the bisazole-based compound of this invention.

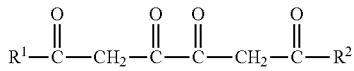

is obtained by reacting a mixture containing haloalkyl acetate and a 2,3-butanedione in the presence of an alkaline sodium salt. The alkaline sodium salt includes, but is not limited to, sodium methylate or sodium ethylate.

Preferably, the reaction step for preparing a bisazole-based compound in which X is nitrogen comprises: reacting oxalyl dihydrazide,

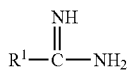

and

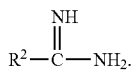

This invention also provides a transition metal complex represented by the following formula (II):

ML¹L²L³       (II)

wherein M is a transition metal;
L¹ represents

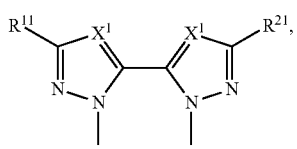

in which X represents C—R³¹ or nitrogen, R¹¹ and R²¹ independently represent a haloalkyl group, and R³¹ represents H or F;

L² and L³ independently represent a dipyridine-based ligand, and at least one of L² and L³ is a dipyridine-based ligand having

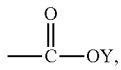

Y representing H, an alkali metal group, a $C_1$ to $C_{12}$ linear alkyl group, a $C_1$ to $C_{12}$ branched alkyl group, or $N(C_4H_9)_4^+$.
L¹ is derived from the aforesaid bisazole-based compound.

Preferably, M is a Group VIII transition metal. More preferably, M is ruthenium or osmium.

Preferably, the haloalkyl group is a $C_1$ to $C_5$ haloalkyl group.

More preferably, the haloalkyl group is $CF_3$, $C_2F_5$, or $C_3F_7$.
Most preferably, the haloalkyl group is $CF_3$.

In an embodiment of this invention, X is C—R³, and R³ is H.

In another embodiment of this invention, X is nitrogen.

Preferably, the dipyridine-based ligand is represented by formula (III):

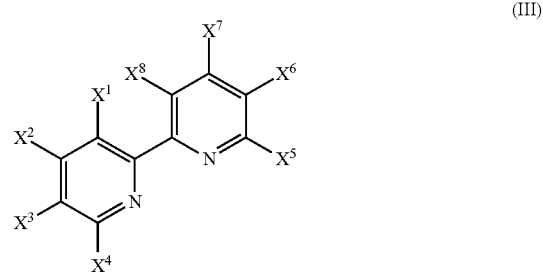

wherein $X^1$, $X^2$, $X^3$, $X^4$, $X^5$, $X^6$, $X^7$, and $X^8$, independently represent hydrogen, halogen, $CF_3$, a $C_1$-$C_{12}$ linear alkyl group, a $C_1$-$C_{12}$ branched alkyl group, a phosphoryl group, a phosphate group, a boric acid group, a borate group, a sulfo group, a sulfonate group,

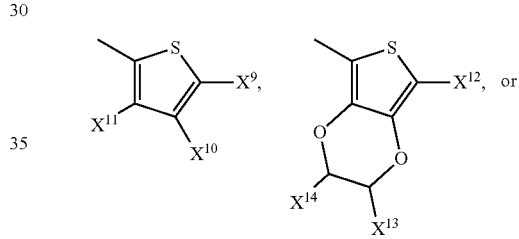

Y representing H, an alkali metal group, a $C_1$ to $C_{12}$ linear alkyl group, a $C_1$ to $C_{12}$ branched alkyl group, or $N(C_4H_9)_4^+$; $X^9$, $X^{10}$, $X^{11}$, $X^{12}$, $X^{13}$, and $X^{14}$ independently representing an organic group.

Preferably, at least two of $X^1$, $X^2$, $X^3$, $X^4$, $X^5$, $X^6$, $X^7$, and $X^8$ are

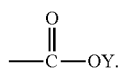

Preferably, at least two of $X^1$, $X^2$, $X^3$, $X^4$, $X^5$, $X^6$, $X^7$, and $X^8$ are —COOH.

The reactants and reaction conditions for the transition metal complex may be selected based on the respective substituted groups. The reaction steps comprise: reacting a ruthenium source or osmium source and a dipyridine-based ligand to form an intermediate; and then reacting the intermediate and the abovementioned bisazole-based compound in the presence of a catalyst under heating to obtain the Group VIII transition metal complex of the present invention. The ruthenium source is dichloro(p-cymene) ruthenium(II) dimer. The osmium source is $Os_3(CO)_{12}$. Preferably, the catalyst is potassium acetate or sodium acetate. After the Group VIII transition metal complex is made, the ester acid functional groups may be hydrolyzed into $CO_2^-$ or COOH through the catalysis of an alkaline reagent. Preferably, the alkaline reagent is a sodium hydroxide (NaOH) solution or a tetrabutyl ammonium hydroxide (TBAOH) solution.

The Group VIII transition metal complex of the present invention is symmetrical in structure and this symmetrical structure enables the absorption peaks of the metal-to-ligand charge transfer (MLCT) effect to be overlapping, thereby improving light absorption for the Group VIII transition metal complex. Moreover, when the Group VIII transition metal complex is applied to a dye-sensitized solar cell, the improved light absorption facilitates usability of sunlight for the dye-sensitized solar cell.

This invention also provides a dye-sensitized solar cell including:

an electrolytic component;

a first electrode disposed in the electrolytic component and including a transparent conductive substrate and a porous film disposed on a surface of the transparent conductive substrate, the porous film absorbing the abovementioned Group VIII transition metal complex; and a second electrode spaced apart from the first electrode and disposed in the electrolytic component.

Examples of the electrolytic component include, but are not limited to, a mixture solution containing 1,3-dimethylimidazolium iodide (DMII, 1.0M), guanidinium thiocyanate (0.1M), lithium iodide (LiI, 0.05M), iodine ($I_2$, 0.03M), and tertbutyl pyridine (0.5M) in a solvent containing acetonitrile and valeronitrile (volume ratio of acetonitrile to valeronitrile is 85:15), and a mixture solution containing 1,3-dimethylimidazolium iodide (1.0M), lithium iodide (0.05M), iodine (0.03M), guanidiniumthiocyanate (0.1M), and N-butyl-1H-benzimidazole (NBB, 0.5M) in 3-methyoxy propanenitrile.

Preferably, the porous film is made of a material selected from titanium dioxide ($TiO_2$), zinc oxide and tin oxide. Preferably, the transparent conductive substrate is made of a flexible polymer material or a rigid material. The flexible polymer material includes, but is not limited to, polyethylene, polypropylene, polyimide, polymethyl methacrylate, polycarbonate, polyethyleneterephthalate, etc. The rigid material includes, but is not limited to, glass. The method for manufacturing the dye-sensitized solar cell is well known in the art and will not be described in detail hereinafter.

EXAMPLES

Preparation of Bisazole-Based Compound

Synthesis Example 1

Oxalyl dihydrazide (1.00 g, 8.5 mmol) and trifluoroacetamidine (2.37 g, 21.2 mmol) were placed in a 150 ml reaction flask, followed by adding 100 ml ethanol to obtain a mixture. The mixture was heated under reflux under a nitrogen gas atmosphere for 24 hours. After the reaction was finished, the mixture was cooled to room temperature. A filtration process was conducted and a white filter cake was collected, followed by washing the white filter cake using deionized water. Next, the filter cake was placed in a 50 ml reaction flask, followed by heating for 2 hours at 280° C. A reduced pressure sublimation process was conducted to obtain a colorless solid (0.968 g, 3.56 mmol, 42% yield).

The spectrum analysis for the colorless solid is: $^{19}F-\{^1H\}$ NMR (470 MHz, $d_6$-dimethyl sulfoxide, 294K), δ(ppm): −65.80 (s, $CF_3$); MS (EI): m/z 272 $[M]^+$. The chemical structure of the colorless solid is

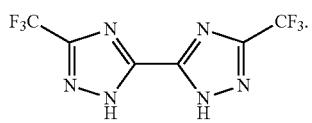 [SMILES: FC(F)(F)c1n[nH]c(-c2nc(C(F)(F)F)n[nH]2)n1]

Synthesis Example 2

Sodium ethylate (0.87 g, 12.79 mmol) and dehydrated tetrahydrofuran (THF, 100 ml) were added into a 50 ml reaction flask, followed by slowly adding ethyl trifluoroacetate (1.816 g, 12.78 mmol) and 2,3-butanedione at 0° C. to obtain a mixture. The mixture was reacted at room temperature for 24 hours. After the reaction was finished, pH of the mixture was adjusted to about 7 using a hydrogen chloride solution (2N), followed by removing tetrahydrofuran by means of reduced pressure distillation to obtain a distilled mixture. Then, the distilled mixture was added with 100 ml ethanol and hydrazine (1.45 g, 29 mmol), followed by heating under reflux for 24 hours under a nitrogen gas atmosphere. After the reaction was finished, ethanol was removed by virtue of reduced pressure distillation. Next, 100 ml ethyl acetate and 100 ml deionized water were added to perform partition extraction, and the ethyl acetate layer was collected and further added with 100 ml deionized water, followed by repeating the partition extraction step three times. The collected ethyl acetate layer was subjected to column chromatography, in which a mixture of ethyl acetate and hexane (ethyl acetate:hexane=1:1) was used as an eluent. Thereafter, recrystallization was conducted using dichloromethane to obtain a white solid product (0.43 g, 28% yield).

The spectrum analysis for the white solid product is: $^{19}F$ (470 MHz, $CDCl_3$, 294 K): δ −62.74 (s, $CF_3$); $^1H$ NMR (400 MHz, $d_6$-acetone, 298K), δ(ppm): 13.53 (s, 2H), 7.16 (s, 2H); MS (EI): m/z 270 $[M]^+$. The chemical structure of the white solid product is

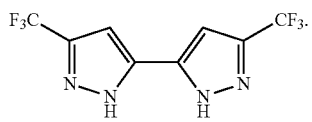 [SMILES: FC(F)(F)c1cc(-c2cc(C(F)(F)F)n[nH]2)[nH]n1]

Preparation of Ruthenium Complex

Example 1

Dichloro(p-cymene) ruthenium(II) dimer (100 mg, 0.163 mmol) and 4,4'-diethoxycarbonyl-2,2'-bipyridine (97.7 mg, 0.326 mmol) were disposed in a 150 ml reaction flask, followed by adding 50 ml methanol and heating at 60° C. for 4 hours under a nitrogen gas atmosphere. After the reaction was finished, the reaction mixture was cooled to room temperature, followed by reduced pressure distillation to remove methanol. Next, the mixture was added with 4,4'-diethoxycarbonyl-2,2'-bipyridine (97.7 mg, 0.326 mmol) and 50 ml dimethylformamide, followed by heating at 140° C. for 4 hours under a dark condition. After the reaction was finished, the reaction mixture was cooled to room temperature, followed by reduced pressure distillation to remove dimethylformamide. Thereafter, the product of Synthesis Example 2 (92.3 mg, 0.342 mmol), sodium acetate (0.134 g, 1.63 mmol) and 50 ml toluene were added in the reaction flask, followed by heating under reflux for 8 hours under a nitrogen gas atmosphere. After the reaction was finished, the mixture was cooled to room temperature and toluene was removed by virtue of reduced pressure distillation. Next, 100 ml dichloromethane and 100 ml deionized water were added to perform partition extraction, and the dichloromethane layer was collected and further added with 100 ml deionized water, followed by repeating the partition extraction step three times. The collected dichloromethane layer was subjected to column chromatography, in which a mixture of ethyl acetate and hexane (ethyl acetate:hexane=1:5) was used as an eluent to obtain a black solid product (0.133 g, 0.1337 mmol, 42% yield). The black solid product (0.1 g, 0.103 mmol) was dissolved in 50 ml acetone, followed by adding 5 ml of a sodium hydroxide solution (2M) and stirring at room temperature for 8 hours. Next, acetone was removed by means of reduced pressure distillation, followed by adding 20 ml deionized water and adjusting pH of the reaction mixture to about 3 using a hydrogen chloride solution (2N). A filtration process was conducted and a filter cake was collected, followed by washing the filter cake using deionized water and dichloromethane to obtain a dark brown solid product (77.8 mg, 0.091 mmol, 88% yield) (hereinafter referred to as ruthenium complex A-1).

The spectrum analysis for the ruthenium complex A-1 is: $^1$H NMR (400 MHz, $d_6$-dimethyl sulfoxide, 294K), δ(ppm): 9.03 (s, 2H), 8.93 (s, 2H), 7.96 (d, $^3J_{HH}$=6 Hz, 2H), 7.91 (d, $^3J_{HH}$=6 Hz, 2H), 7.82 (d, $^3J_{HH}$=6 Hz, 2H), 7.67 (d, $^3J_{HH}$=6 Hz, 2H), 6.67 (s, 2H); $^{19}$F-{$^1$H} NMR (470 MHz, $d_6$-dimethyl sulfoxide, 294K), δ(ppm): −57.59 (s, CF$_3$); MS (FAB): m/z 858 (M)$^+$. The element analysis data is: C, 43.34%; N, 12.34%; H, 2.74%.

The chemical structure of the ruthenium complex A-1 is

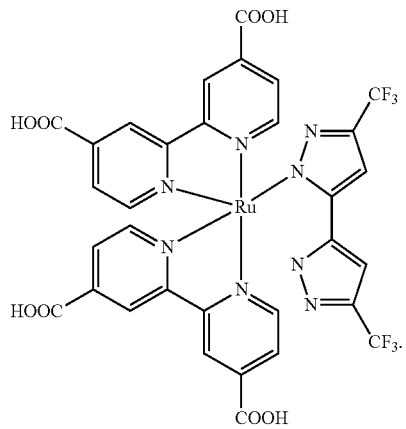

Example 2

Dichloro(p-cymene) ruthenium(II) dimer (100 mg, 0.163 mmol) and 4,4'-diethoxycarbonyl-2,2'-bipyridine (97.7 mg, 0.326 mmol) were disposed in a 150 ml reaction flask, followed by adding 50 ml methanol and heating at 60° C. for 4 hours under a nitrogen gas atmosphere. After the reaction was finished, the reaction mixture was cooled to room temperature, followed by reduced pressure distillation to remove methanol. Next, the mixture was added with 4,4'-diethoxycarbonyl-2,2'-bipyridine (97.7 mg, 0.326 mmol) and 50 ml dimethylformamide, followed by heating at 140° C. for 4 hours under a dark condition. After the reaction was finished, the reaction mixture was cooled to room temperature, followed by reduced pressure distillation to remove dimethylformamide. Thereafter, the product of Synthesis Example 1

(93.0 mg, 0.342 mmol), sodium acetate (0.134 g, 1.63 mmol) and 50 ml toluene were added in the reaction flask, followed by heating under reflux for 8 hours under a nitrogen gas atmosphere. After the reaction was finished, the mixture was cooled to room temperature and toluene was removed by virtue of reduced pressure distillation. Next, 100 ml dichloromethane and 100 ml deionized water were added to perform partition extraction, and the dichloromethane layer was collected and further added with 100 ml deionized water, followed by repeating the partition extraction step three times. The collected dichloromethane layer was subjected to column chromatography, in which a mixture of ethyl acetate and hexane (ethyl acetate:hexane=1:1) was used as an eluent to obtain a black solid product (0.152 g, 0.156 mmol, 48% yield). The black solid product (0.1 g, 0.103 mmol) was dissolved in 50 ml acetone, followed by adding 5 ml of a sodium hydroxide solution (2M) and stirring at room temperature for 8 hours. Next, acetone was removed by means of reduced pressure distillation, followed by adding 20 ml deionized water and adjusting pH of the reaction mixture to about 3 using a hydrogen chloride solution (2N). A filtration process was conducted and a filter cake was collected, followed by washing the filter cake using deionized water and dichloromethane to obtain a dark brown solid product (76.97 mg, 0.090 mmol, 87% yield) (hereinafter referred to as ruthenium complex A-2).

The spectrum analysis for the ruthenium complex A-2 is: $^1$H NMR (400 MHz, $d_6$-dimethyl sulfoxide, 294K), δ(ppm): 9.12 (s, 2H), 9.09 (s, 2H), 8.03~8.01 (m, 4H), 7.90 (d, $^3J_{HH}$=5.6 Hz, 2H), 7.75 (d, $^3J_{HH}$=5.6 Hz, 2H); $^{19}$F-{$^1$H} NMR (470 MHz, $d_6$-dimethyl sulfoxide, 294K), δ(ppm): −61.62 (s, CF$_3$); MS (FAB): m/z 860 (M)$^+$.

The chemical structure of the ruthenium complex A-2 is

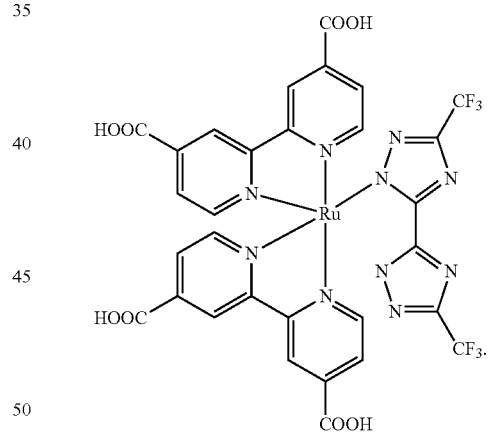

Example 3

Dichloro(p-cymene) ruthenium(II) dimer (100 mg, 0.163 mmol) and 4,4'-bis(5-hexylthiophen-2-yl)-2,2'-bipyridine (159 mg, 0.326 mmol) were disposed in a 150 ml reaction flask, followed by adding 50 ml methanol and heating at 60° C. for 4 hours under a nitrogen gas atmosphere. After the reaction was finished, the reaction mixture was cooled to room temperature, followed by reduced pressure distillation to remove methanol. Next, the mixture was added with 4,4'-diethoxycarbonyl-2,2'-bipyridine (97.879 mg, 0.326 mmol) and 50 ml dimethylformamide, followed by heating at 140° C. for 4 hours under a dark condition. After the reaction was finished, the reaction mixture was cooled to room temperature, followed by reduced pressure distillation to remove dimethylformamide. Thereafter, the product of Synthesis Example 2 (92.5 mg, 0.343 mmol), sodium acetate (0.134 g, 1.63 mmol) and 50 ml toluene were added in the reaction flask, followed by heating under reflux for 8 hours under a nitrogen gas atmosphere. After the reaction was finished, the mixture was cooled to room temperature and toluene was removed by virtue of reduced pressure distillation. Next, 100 ml dichloromethane and 100 ml deionized water were added to perform partition extraction, and the dichloromethane layer was collected and further added with 100 ml deionized water, followed by repeating the partition extraction step three times. The collected dichloromethane layer was subjected to column chromatography, in which a mixture of ethyl acetate and hexane (ethyl acetate:hexane=1:1) was used as an eluent to obtain a black solid product (0.173 g, 0.15 mmol, 46% yield).

The black solid product (0.1 g, 0.086 mmol) was dissolved in 50 ml acetone, followed by adding 5 ml of a sodium hydroxide solution (2M) and stirring at room temperature for 8 hours. Next, acetone was removed by means of reduced pressure distillation, followed by adding 20 ml deionized water and adjusting pH of the reaction mixture to about 3 using a hydrogen chloride solution (2N). A filtration process was conducted and a filter cake was collected, followed by washing the filter cake using deionized water and dichloromethane to obtain a dark brown solid product (80.9 mg, 0.073 mmol, 85% yield) (hereinafter referred to as ruthenium complex A-3).

The spectrum analysis for the ruthenium complex A-3 is: $^1$H NMR (400 MHz, $d_6$-dimethyl sulfoxide, 294K), δ(ppm): 8.77 (s, 2H), 8.73 (s, 1H), 8.68 (s, 1H), 7.87 (br.s, 1H), 7.77 (d, $^3J_{HH}$=6 Hz, 1H), 7.72 (d, $^3J_{HH}$=6 Hz, 1H), 7.62~7.49 (m, 6H), 7.32 (br.s 1H), 6.95 (m, 2H), 6.55 (s, 1H), 6.53 (s, 1H), 2.84~2.80 (m, 6H), 1.29~1.26 (m, 16H), 0.85~0.84 (m, 6H); $^{19}$F-{$^1$H} NMR (470 MHz, $d_6$-dimethyl sulfoxide, 298K), δ(ppm): −57.3 (s, $CF_3$), −57.4 (s, $CF_3$).

The chemical structure of the ruthenium complex A-3 is

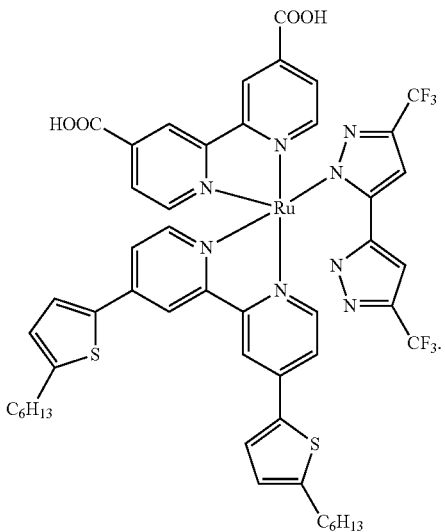

Example 4

Dichloro(p-cymene) ruthenium(II) dimer (100 mg, 0.163 mmol) and 4,4'-bis(5-hexylthiophen-2-yl)-2,2'-bipyridine (159 mg, 0.326 mmol) were disposed in a 150 ml reaction flask, followed by adding 50 ml methanol and heating at 60° C. for 4 hours under a nitrogen gas atmosphere. After the reaction was finished, the reaction mixture was cooled to room temperature, followed by reduced pressure distillation to remove methanol. Next, the mixture was added with 4,4'-diethoxycarbonyl-2,2'-bipyridine (97.879 mg, 0.326 mmol) and 50 ml dimethylformamide, followed by heating at 140° C. for 4 hours under a dark condition. After the reaction was finished, the reaction mixture was cooled to room temperature, followed by reduced pressure distillation to remove dimethylformamide. Thereafter, the product of Synthesis Example 1 (93.0 mg, 0.342 mmol), sodium acetate (0.134 g, 1.63 mmol) and 50 ml toluene were added in the reaction flask, followed by heating under reflux for 8 hours under a nitrogen gas atmosphere. After the reaction was finished, the mixture was cooled to room temperature and toluene was removed by virtue of reduced pressure distillation. Next, 100 ml dichloromethane and 100 ml deionized water were added to perform partition extraction, and the dichloromethane layer was collected and further added with 100 ml deionized water, followed by repeating the partition extraction step three times. The collected dichloromethane layer was subjected to column chromatography, in which a mixture of ethyl acetate and hexane (ethyl acetate:hexane=1:1) was used as an eluent to obtain a black solid product (0.171 g, 0.147 mmol, 43% yield). The black solid product (0.1 g, 0.086 mmol) was dissolved in 50 ml acetone, followed by adding 5 ml of a sodium hydroxide solution (2M) and stirring at room temperature for 8 hours. Next, acetone was removed by means of reduced pressure distillation, followed by adding 20 ml deionized water and adjusting pH of the reaction mixture to about 3 using a hydrogen chloride solution (2N). A filtration process was conducted and a filter cake was collected, followed by washing the filter cake using deionized water and dichloromethane to obtain a dark brown solid product (79.9 mg, 0.072 mmol, 84% yield) (hereinafter referred to as ruthenium complex A-4).

The spectrum analysis for the ruthenium complex A-4 is: $^1$H NMR (400 MHz, $d_6$-dimethyl sulfoxide, 294K), δ(ppm): 9.07 (s, 1H), 9.06 (s, 1H), 8.92 (s, 1H), 8.91 (s, 1H), 8.18 (d, $^3J_{HH}$=6 Hz, 1H), 8.10~7.90 (m, 4H), 7.80 (d, $^3J_{HH}$=5.8 Hz, 1H), 7.76 (d, $^3J_{HH}$=5.8 Hz, 1H), 7.59 (d, $^3J_{HH}$=6 Hz, 1H), 7.52 (d, $^3J_{HH}$=6 Hz, 1H), 7.43 (d, $^3J_{HH}$=4.4 Hz, 1H), 7.05 (m, 2H), 2.85 (q, $^3J_{HH}$=8 Hz, 4H), 1.64 (q, $^3J_{HH}$=8 Hz, 4H), 1.28~1.26 (m, 12H), 0.86~0.84 (m, 6H); $^{19}$F-{$^1$H} NMR (470 MHz, $d_6$-dimethyl sulfoxide, 294K), δ(ppm): −61.62 (s, $CF_3$), −61.59 (s, $CF_3$); MS (FAB): m/z 1104 (1105) [M+1]$^+$.

The chemical structure of the ruthenium complex A-4 is

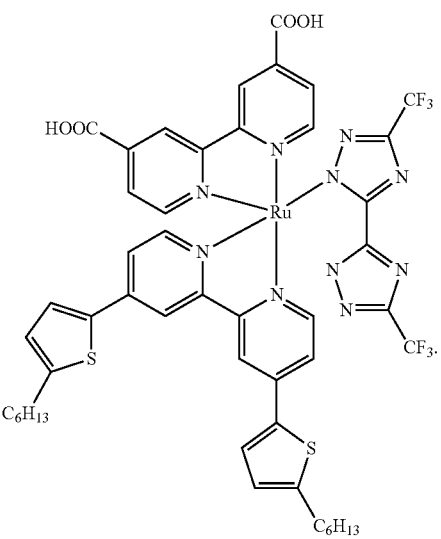

Preparation of Osmium Complex

Example 5

Os$_3$(CO)$_{12}$ (0.2 g, 0.221 mmol), 4,4'-di-tert-butyl-2,2'-bipyridine (173 mg, 0.684 mmol) and the product of Synthesis Example 1 (185 mg, 0.684 mmol) were disposed in a 150 ml reaction flask, followed by adding 50 ml diethylene glycol monomethyl ether and heating at 180° C. for 24 hours under a nitrogen gas atmosphere. After the reaction was finished, the reaction mixture was cooled to room temperature, followed by reduced pressure distillation to remove diethylene glycol monomethyl ether. Next, the mixture was subjected to column chromatography, in which a mixture of ethyl acetate and hexane (ethyl acetate:hexane=1:1) was used as an eluent. Thereafter, recrystallization was conducted using dichloromethane and hexane to obtain a yellow solid product (0.162 g, 0.205 mmol, 31% yield). The yellow solid product (0.1 g, 0.127 mmol) was dissolved in diethylene glycol monomethyl ether, followed by adding trimethylamine N-oxide (20 mg, 0.267 mmol) and stirring at room temperature for 1 hour. Thereafter, the mixture was added with 4,4'-diethoxycarbonyl-2,2'-bipyridine (41.98 mg, 0.14 mmol), followed by heating under reflux for 24 hours under a nitrogen gas atmosphere. Next, diethylene glycol monomethyl ether was removed by means of reduced pressure distillation. Thereafter, the mixture was subjected to column chromatography, in which a mixture of ethyl acetate and hexane (ethyl acetate: hexane=1:2) was used as an eluent to obtain a black solid product (39.6 mg, 0.041 mmol, 41.9% yield).

The black solid product (0.1 g, 0.103 mmol) was dissolved in 50 ml acetone, followed by adding 5 ml of a sodium hydroxide solution (2M) and stirring at room temperature for 8 hours. Next, acetone was removed by means of reduced pressure distillation, followed by adding 20 ml deionized water and adjusting pH of the reaction mixture to about 3 using a hydrogen chloride solution (2N). A filtration process was conducted and a filter cake was collected, followed by washing the filter cake using deionized water and dichloromethane to obtain a dark brown solid product (86 mg, 0.088 mmol, 86% yield) (hereinafter referred to as osmium complex A-5).

The spectrum analysis for the osmium complex A-5 is: $^1$H NMR (400 MHz, CDCl$_3$, 294K), δ(ppm): 8.99 (s, 1H), 8.97 (s, 1H), 8.74 (s, 1H), 8.66 (s, 1H), 7.98 (d, $^3J_{HH}$=6 Hz, 1H), 7.95 (d, $^3J_{HH}$=6 Hz, 1H), 7.68 (d, $^3J_{HH}$=5.6 Hz, $^1$H), 7.65 (d, $^3J_{HH}$=4.8 Hz, 1H), 7.52 (d, $^3J_{HH}$=6.4 Hz, $^1$H), 7.42 (d, $^3J_{HH}$=6 Hz, 1H), 7.37 (d, $^3J_{HH}$=6 Hz, 1H), 7.27 (d, $^3J_{HH}$=4.8 Hz, 1H), 1.40 (s, 9H), 1.34 (S, 9H); $^{19}$F-{$^1$H} NMR (470 MHz, d$_5$-dimethyl sulfoxide, 294K), δ(ppm): −61.55 (s, CF$_3$), −61.8 (s, CF$_3$); MS (FAB): m/z 974 [M]$^+$.

The chemical structure of the osmium complex A-5 is

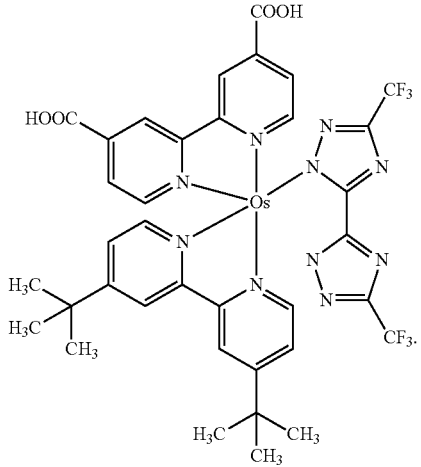

Comparative Example

N719 dye was commercially available from Solaronix SA Co., Switzerland, model no.: Ruthenizer 535-bisTBA. Before the following tests were conducted, the concentration of N719 dye was adjusted to 0.3 mM using absolute alcohol, followed by adding chenodeoxycholic acid (CDCA, 20 nM).

[Tests]

1. Measurement of Molar Extinction Coefficient:

Each of the ruthenium complexes of Examples 1~4, the osmium complex of Example 5 and N719 dye of Comparative Example was dissolved in dimethylformamide, followed by measuring molar extinction coefficients thereof using a UV-Visible Spectrophotometer (Hitachi Spectrophotometer; Model no.: U-3900).

2. Measurement of Redox Potential

Each of the ruthenium complexes of Examples 1~4, the osmium complex of Example 5 and N719 dye of Comparative Example was dissolved in dimethylformamide containing tetrabutylammonium hexafluorophosphate (TBAPF$_6$, 0.1M). The redox potential was measured by a cyclic voltammetry measurement using an electrochemical analyzer (CH Instruments; Model no.: Electrochemical Analyzer CHI621a), in which Fc/Fc$^+$ was used as an internal standard, Ag/AgNO$_3$ was used as a reference electrode, Pt was used as an auxiliary electrode, glassy carbon was used as a working electrode and a scanning speed was 20 mVs$^{-1}$. The obtained potential can be converted to NHE potential by adding 0.630V. The $E_{0-0}$ value was estimated from the intersection of absorption and emission spectra.

3. Measurement of Photoelectric Conversion Efficiency

It is noted that the manufacturing process of a dye-sensitized solar cell is well known in the art and the following examples are used for illustration, and should not be construed as limiting the implementation of the present invention.

To manufacture the dye-sensitized solar cell, a slurry containing titanium dioxide nanoparticles was printed on a conductive glass substrate, followed by sintering in a high temperature furnace to obtain a sintered substrate with a total thickness of 18 micrometers. Next, the sintered substrate was immersed in a titanium tetrachloride aqueous solution (40 mM) and was placed in an oven at 75° C. for 30 minutes, followed by rinsing with deionized water and ethanol to form a conductive substrate containing titanium dioxide. Six conductive substrates containing titanium dioxide were immersed respectively in solutions containing the ruthenium complexes of Examples 1~4, the osmium complex of Example 5 of the present invention and the ruthenium complex of Comparative Example at room temperature for 18 hours, followed by removing from the solutions and washing with absolute alcohol to form six first electrodes.

A chloroplatinic acid solution in isopropanol (10 μl, 5 mM) was dropped onto each of six fluoride-doped tin oxide conductive glasses, followed by thermal cracking at 450° C. for 15 minutes for reduction to platinum metals. Six second electrodes were thus obtained.

The first and second electrodes were packaged in pairs using a hot melting polymer film, and an electrolytic component was injected into pre-drilled small holes in the second electrodes. Next, the small holes were sealed using the hot melting polymer film and small pieces of glass, thereby obtaining six dye-sensitized solar cells. The electrolytic component is a mixture solution containing 1,3-dimethylimidazolium iodide (1.0M), guanidinium thiocyanate (0.1M), lithium iodide (0.05M), iodine (0.03M), and tertbutyl pyridine (0.5M) in a solvent containing acetonitrile and valeronitrile (volume ratio of acetonitrile to valeronitrile is 85:15).

The dye-sensitized solar cells were irradiated by a solar simulator (150 W xenon lamp; Class A, Newport Oriel; Model no.: 91159) that provides a simulation light with air mass (AM) 1.5 Global radiation and an intensity of 100 mW/cm$^2$. An external voltage was applied to each of the dye-sensitized solar cells using a digital electrometer (Keithley; Model no.: 2400), and the currents thereof were recorded. Data were collected to plot a graph of voltage vs. current density. In this graph of voltage vs. current density, $V_{oc}$ which is an open circuit voltage when current density is 0 and $J_{sc}$ which is a short circuit current value when a voltage is 0 were obtained to evaluate the photoelectric conversion efficiency. Specifically, the photoelectric conversion efficiency is obtained by dividing the maximum value of the product of the voltage and the current density by the incident light intensity.

TABLE 1

| Example | E1 | E2 | E3 | E4 | E5 | CE |
|---|---|---|---|---|---|---|
| Yield (%) | 88 | 87 | 85 | 84 | 86 | — |
| Eox (V vs NHE) | 0.94 | 1.18 | 0.77 | 1.06 | 0.69 | 1.07 |
| E0 – 0 (V vs NHE) | 1.93 | 1.97 | 1.74 | 1.82 | 1.47 | 1.96 |
| E = Eox – E0 – 0 (V) | −0.99 | −0.79 | −0.97 | −0.76 | −0.78 | −0.89 |
| JSC (mA · cm$^{-2}$) | 17.36 | 14.95 | 13.25 | 16.65 | 12.2 | 17.32 |
| VOC (V) | 0.74 | 0.74 | 0.72 | 0.77 | 0.55 | 0.73 |
| Fill factor (FF) | 0.726 | 0.727 | 0.726 | 0.707 | 0.588 | 0.714 |
| Photoelectric conversion efficiency (η, %) | 9.32 | 8.05 | 6.93 | 9.07 | 3.95 | 9.03 |

From Table 1, it is revealed that the Group VIII transition metal complex of the present invention has a yield of above 80% and is a neutral complex, indicating that the ruthenium complex of the present invention can be mass-produced and applied to the industry.

At present, N719 has been widely applied to the dye on the dye-sensitized solar cell. From FIG. 1, it is revealed that the absorption of the ruthenium complexes of Examples 1~5 of the present invention in the near infrared region is comparable to that of the N719 dye of Comparative example. In addition, because N719 includes thiocyanate ligands having weaker ligand bonding strength, chelation of the ligands with ruthenium is weak and unstable under the light and heat effect, so that N719 is liable to decompose during operation of the dye-sensitized solar cell, thereby resulting in poor photoelectric conversion efficiency and short lifespan of the dye-sensitized solar cell. However, since there is no thiocyanate ligand in the Group VIII transition metal complex of the present invention, the dye-sensitized solar cell composed of the Group VIII transition metal complex of the present invention would exhibit improved efficiency and longer lifespan.

In addition, from the preparation processes and the structure analysis data of Examples 1~5, it is evident that the Group VIII transition metal complex of the present invention can be isolated without adding the complexing counterions. Further, as mentioned above, by virtue of the haloalkyl group on the bisazole-based compound of this invention, no structural isomer is generated.

In addition, the energy level potential of the highest occupied molecular orbital of the Group VIII transition metal complexes of Examples 1, 2 and 4 are 0.94V, 1.18V and 1.06V, respectively. This indicates that the energy level potential of the highest occupied molecular orbital of the Group VIII transition metal complex of the present invention can be increased by means of the bisazole-based compound. Therefore, the Group VIII transition metal complex of the present invention can match the redox potential of the electrolytic component to achieve optimum regeneration efficiency.

To sum up, with the bisazole-based compound of the present invention, the Group VIII transition metal complex is capable of maintaining electric neutrality, and the energy level potential of the highest occupied molecular orbital thereof can be increased so that the transition metal complex exhibits better regeneration efficiency. In addition, the Group VIII transition metal complex is relatively easy to purify and has a high yield, and no structural isomer would be formed so that the transition metal complex of the present invention can be mass-produced.

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

What is claimed is:

1. A bisazole-based compound represented by formula (I):

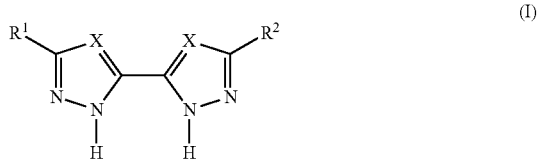

(I)

wherein X represents C—R$^3$ or nitrogen, R$^1$ and R$^2$ independently represent a haloalkyl group, and R$^3$ represents H or F.

2. The bisazole-based compound of claim 1, wherein the haloalkyl group is a C$_1$ to C$_5$ haloalkyl group.

3. The bisazole-based compound of claim 1, wherein the haloalkyl group is CF$_3$, C$_2$F$_5$, or C$_3$F$_7$.

4. The bisazole-based compound of claim 1, wherein X is nitrogen.

5. A transition metal complex represented by formula (II):

wherein M is selected from the group consisting of ruthenium and osmium;

L$^1$ represents

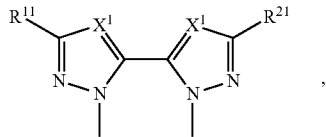

, in which X represents C—R$^{31}$ or nitrogen, R$^{11}$ and R$^{21}$ independently represent a haloalkyl group, and R$^{31}$ represents H or F;

L$^2$ and L$^3$ independently represent a dipyridine-based ligand, and at least one of L$^2$ and L$^3$ is a dipyridine-based ligand having

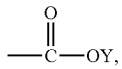

Y representing H, an alkali metal group, a $C_1$ to $C_{12}$ linear alkyl group, a $C_1$ to $C_{12}$ branched alkyl group, or $N(C_4H_9)_4^+$.

6. The transition metal complex of claim 5, wherein M is ruthenium.

7. The transition metal complex of claim 5, wherein M is osmium.

8. The transition metal complex of claim 5, wherein the dipyridine-based ligand is represented by formula (III)

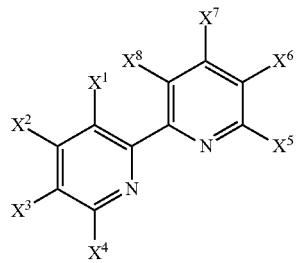

wherein $X^1$, $X^2$, $X^3$, $X^4$, $X^5$, $X^6$, $X^7$, and $X^8$ independently represent hydrogen, halogen, $CF_3$, a $C_1$-$C_{12}$ linear alkyl group, a $C_1$-$C_{12}$ branched alkyl group, a phosphoryl group, a phosphate group, a boric acid group, a borate group, a sulfo group, a sulfonate group,

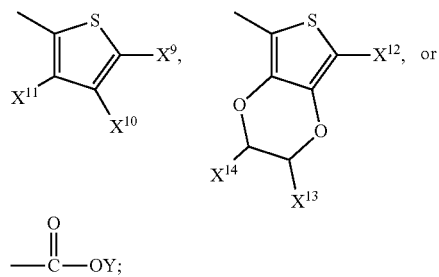

Y representing H, an alkali metal group, a $C_1$ to $C_{12}$ linear alkyl group, a $C_1$ to $C_{12}$ branched alkyl group, or $N(C_4H_9)_4^+$; $X^9$, $X^{10}$, $X^{11}$, $X^{12}$, $X^{13}$, and $X^{14}$ independently representing an organic group.

9. The transition metal complex of claim 8, wherein at least two of $X^1$, $X^2$, $X^3$, $X^4$, $X^5$, $X^6$, $X^7$, and $X^8$ are

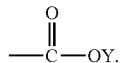

10. The transition metal complex of claim 8, wherein at least two of $X^1$, $X^2$, $X^3$, $X^4$, $X^5$, $X^6$, $X^7$, and $X^8$ are —COOH.

11. The bisazole-based compound of claim 1, wherein $R^1$ is $CF_3$, $R^2$ is $CF_3$ and $R^3$ is H.

12. The transition metal complex of claim 5, wherein $R^{11}$ is $CF_3$, $R^{21}$ is $CF_3$, $R^{31}$ is H,

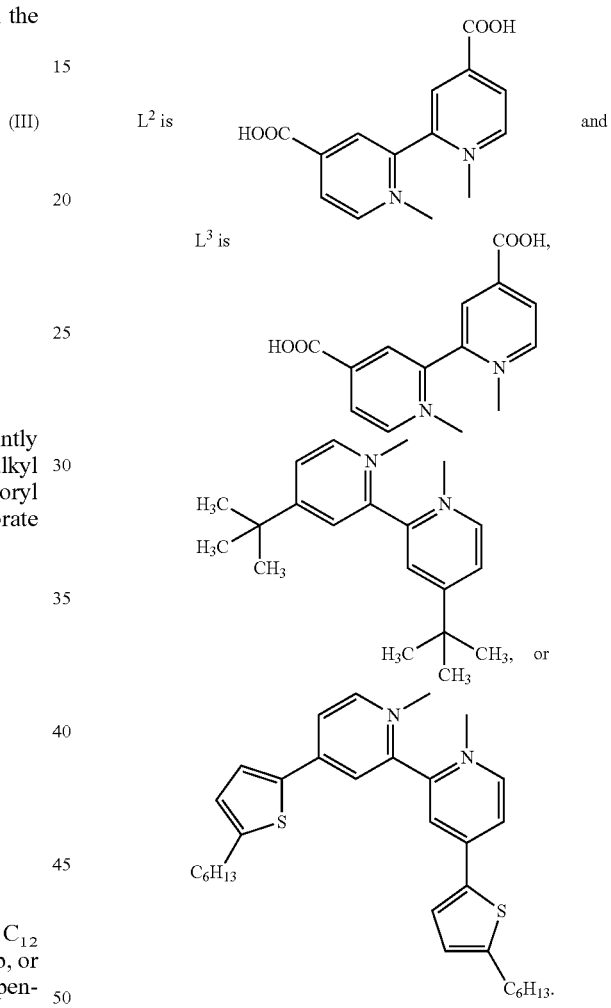

* * * * *